United States Patent [19]

Baxamusa et al.

[11] 4,183,873
[45] * Jan. 15, 1980

[54] LIQUID PHASE FLUORINATION PROCESS

[75] Inventors: Yusuf A. Baxamusa, Tonawanda; Stephen Robota, North Tonawanda, both of N.Y.

[73] Assignee: Hooker Chemicals & Plastics Corp., Niagara Falls, N.Y.

[ * ] Notice: The portion of the term of this patent subsequent to Jul. 4, 1995, has been disclaimed.

[21] Appl. No.: 912,629

[22] Filed: Jun. 5, 1978

Related U.S. Application Data

[63] Continuation-in-part of Ser. No. 737,626, Nov. 1, 1976, Pat. No. 4,098,832.

[51] Int. Cl.² ............................................. C07C 25/14
[52] U.S. Cl. .................................................. 260/651 F
[58] Field of Search ..................................... 260/651 F

[56] References Cited

U.S. PATENT DOCUMENTS

| | | | |
|---|---|---|---|
| 3,131,226 | 4/1964 | Olstowski et al. ................. | 260/653.8 |
| 3,435,082 | 3/1969 | Ager ................................... | 260/653.8 |
| 3,859,372 | 1/1975 | Robota ............................. | 260/651 F |
| 4,079,089 | 3/1978 | Klauke .............................. | 260/651 F |
| 4,079,090 | 3/1978 | Büttner et al. .................... | 260/651 F |
| 4,093,669 | 6/1978 | Klauke et al. ..................... | 260/651 F |

Primary Examiner—C. Davis

Attorney, Agent, or Firm—Peter F. Casella; William J. Crossetta, Jr.; Arthur S. Cookfair

[57] ABSTRACT

A process for the preparation of compounds of the formula:

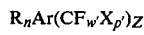

$$R_nAr(CF_{w'}X_{p'})_Z$$

comprises contacting compounds of the formula:

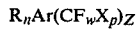

$$R_nAr(CF_wX_p)_Z$$

in the liquid phase, with hydrogen fluoride in the presence of molybdenum chloride wherein Ar is aryl
R is a substituent on the aryl nucleus selected from the group consisting of aryl, substituted aryl, halogen, alkyl, alkoxy, substituted alkyl, and substituted alkoxy;
n is 0 to 9;
X is halogen atom other than fluorine;
w is 0 to 2;
p is 1 to 3;
w' is 1 to 3, and is greater than w;
p' is 0 to 2, and is less than p;
w+p is 3;
w'+p' is 3;
Z is 1–10; and
the maximum value of n+Z is 10.

16 Claims, No Drawings

LIQUID PHASE FLUORINATION PROCESS

This is a continuation-in-part of Ser. No. 737,626, filed Nov. 1, 1976 and now U.S. Pat. No. 4,098,832.

BACKGROUND OF THE INVENTION

This invention relates to a process for the preparation of organic fluoride compounds, and in particular, to a process for the liquid phase replacement of halogen atoms with fluorine in organic compounds.

A variety of fluorination processes are known wherein fluorine replaces substituents of organic compounds, such as halogen atoms, hydrogen atoms, and the like. Such known processes include both vapor phase fluorination reactions and liquid phase fluorination reactions. Typically, such processes involve the reaction of an organic halide with hydrogen fluoride, sometimes in the presence of catalyst, such as antimony pentachloride, at atmospheric or super-atmospheric pressures. Many of the known processes, while suitable for laboratory investigations and experiments, are unsuitable for commercial use for various reasons, such as the low purity of product obtained, the high cost of equipment which must be employed, or the need for frequent replacement of the catalyst, due to loss or deactivation. One of the common difficulties encountered in vapor phase fluorination reactions results from the highly exothermic nature of such reactions. The heat evolved frequently results in a temperature rise sufficient to cause thermal decomposition of some of the organic starting materials and a resultant carbonization of the catalyst. Furthermore, such vapor phase reactions commonly require the use of substantial stoichiometric excess of hydrogen fluoride with the attendant problem of disposal of the hazardous hydrogen fluoride containing effluent gases.

Some of the problems associated with vapor phase fluorination processes may be avoided through the use of liquid phase fluorination. However, although atmospheric liquid phase fluorination processes are known and are used in laboratory preparations, they have not received widespread acceptance for larger scale commercial use for various reasons. Heretofore, the most widely used catalyst for liquid phase fluorinations has been antimony pentachloride or a mixture of antimony pentachloride and antimony trichloride. However, antimony chlorides, although highly effective in the catalysis of fluorination reactions, are very volatile materials. To avoid the problems associated with the volatility of antimony chlorides, such fluorination reactions are often carried out in closed systems under superatmospheric pressure, necessitating the use of pressure equipment. In addition it has been found that to obtain desirably high yields, antimony chloride catalysts must be employed in relatively large concentrations. Thus, although antimony chlorides provide an effective catalyst for fluorination reactions, a need exists for a still more effective catalyst that will overcome the aforementioned disadvantages.

It is an object of the present invention to provide an improved process for the liquid phase fluorination of organic halides. It is a further object to provide an improved catalyst for fluorination reactions that is relatively low in cost, of low volatility, and that may be effectively employed at relatively low concentrations. It is a further object to provide an improved process for the fluorination of organic halides in the liquid phase by reaction with hydrogen fluoride, wherein the hydrogen fluoride may be employed in either concentrated or dilute form. It is a still further object to provide a multi-step fluorination process comprising both a vapor phase and a liquid phase reaction wherein substantial improvements in the effective utilization of hydrogen fluoride reactant are achieved and the amount of hydrogen fluoride waste product is substantially reduced.

SUMMARY OF THE INVENTION

In accordance with the present invention, there is provided a process for the preparation of fluorinated aromatic compounds which comprises reacting a halomethyl aromatic compound, wherein the halo is other than fluorine, with a fluorinating agent in the presence of a catalytic amount of molybdenum pentachloride. The halomethyl aromatic compound may also contain stable ring constituents, such as halogen, alkyl, alkoxy, substituted alkyl and the like, or other substituents that will not adversely affect the reaction.

In particular, this invention is directed to a process for the preparation of compounds of the formula:

$$R_nAr(CF_{w'}X_{p'})_Z$$

which comprises contacting compounds of the formula:

$$R_nAr(CF_wX_p)_Z$$

in the liquid phase, with hydrogen fluoride in the presence of molybdenum pentachloride wherein
  Ar is aryl;
  R is a substituent on the aryl nucleus selected from the group consisting of aryl, substituted aryl, halogen, alkyl, alkoxy and substituted alkyl;
  n is 0 to 9;
  X is halogen atom other than fluorine;
  w is 0 to 2;
  p is 1 to 3;
  w' is 1 to 3, and is greater than w;
  p' is 0 to 2, and is less than p;
  w+p is 3;
  w'+p' is 3;
  Z is 1-10; and
  the maximum value of n+Z is 10.

The designation Ar or aryl represent an aromatic structure such as benzene, naphthalene, anthracene and the like, preferably of up to 14 carbon atoms. The preferred compounds prepared in accordance with this invention are those of the above formula wherein Ar is benzene.

Among the R substituents encompassed within the formula shown above, are alkyl radicals of from 1 to about 20 carbon atoms, and preferably of from 1 to about 12 carbon atoms, such as methyl, ethyl, propyl, butyl, amyl, octyl, decyl, dodecyl, pentadecyl, eicosyl, as well as their various isomer forms, such as isopropyl and isobutyl, said alkyl radical being a monovalent radical derivable from an aliphatic hydrocarbon alkane by the removal of 1 hydrogen atom; substituted alkyl of from 1 to about 30 carbon atoms and preferably of from 1 to about 15 carbon atoms, said alkyl group being substituted by one or more of aryl, substituted aryl, and the like; alkoxy and substituted alkoxy of from 1 to about 20 carbon atoms, and preferably of from 1 to about 12 carbon atoms, such as methoxy, ethoxy, propoxy, butoxy, pentoxy, octoxy, dodecoxy, pentadecoxy, eicosoxy, as well as their various isomer forms, such as iso-propoxy, iso-butoxy, and the like; and halogen. Various other R substituents may be present on the haloalkyl aromatic compound reactants and corresponding products will be obtained. The number (n) of R substituents present on the aromatic nucleus is from 0 to 9 and preferably from 0 to 5. Where n is more than 1, the R substituents may be the same or different. The number (Z) substituents on the aromatic nucleus is from 1 to 10 and preferably 1 or 2. The maximum number of substituents (n+Z) is equal to the total number of positions available on the aromatic nucleus. Thus when Ar is benzene, the maximum value of n+Z is 6, and in this instance, for example, if the value of n is 3, the maximum value of Z will be 3. Similarly when Ar is naphthalene, the maximum value of n+Z is 8 and when Ar is anthracene the maximum value of n+Z is 10. The preferred compounds which may be fluorinated in accordance with this invention are those of the above formula wherein Ar is benzene, R is chlorine, n is 0 to 2, and Z is 1 or 2.

DESCRIPTION OF PREFERRED EMBODIMENTS

In a preferred embodiment the present invention is directed to a process for fluorination of compounds of the above formula wherein Ar is benzene; Z is 1 or 2; R is a halogen, preferably fluorine, chlorine, or bromine and n is 0 to 2. Such starting compounds may be characterized by the formula:

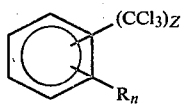

wherein Z is 1 or 2, preferably 2, R is halogen, preferably chlorine, and n is 0 to 2, preferably 0. In accordance with this invention such compounds are fluorinated by reaction with hydrogen fluoride, preferably in an amount less than the stoichiometric amount necessary to completely replace the chlorine atoms on the side chain(s) with fluorine in the presence of molybdenum pentachloride. The fluorination occurs on the side chain of the aromatic compound with the replacement of the halogen atoms thereof by fluorine. The degree of fluorination will depend in part on the amount of fluorinating agent supplied to the reaction and the length of time the reaction is carried out. Thus, for example, depending on these and other conditions of reactions described hereinbelow, a compound of the above formula wherein Z is 1, such as

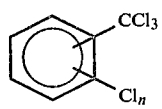

in the liquid phase, may be reacted with hydrogen fluoride, in the presence of molybdenum pentachloride to prepare

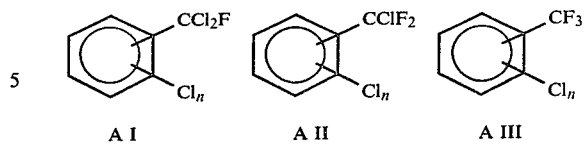

or mixtures thereof. Similarly, a compound of the above formula wherein Z is 2, such as,

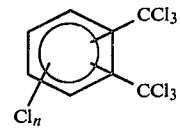

wherein n is 0 to 2, is reacted with hydrogen fluoride in the presence of molybdenum pentachloride to prepare compounds such as:

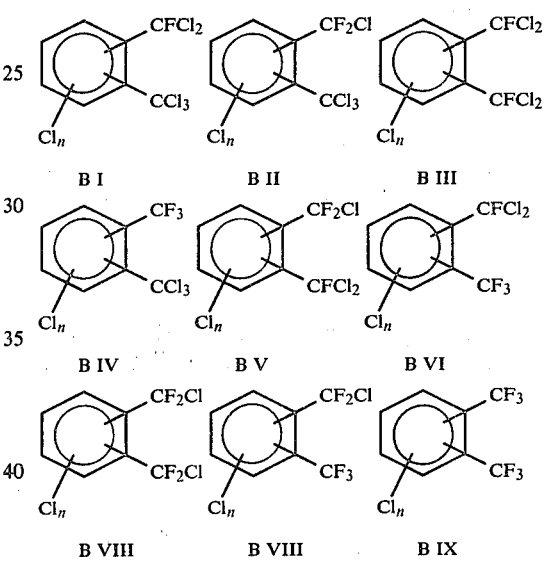

or various mixtures of such fluorinated or partially fluorinated compounds. Alternatively, partially fluorinated compounds, such as compounds A I and A II may be employed as starting materials and further fluorinated by the process of this invention to produce higher fluorinated compounds such as compounds A II and A III. Similarly, partially fluorinated compounds such as B I through B VIII may be employed as starting materials and further fluorinated by the process of this invention to produce higher fluorinated compounds such as B II through B IX.

The temperature of the reaction may vary considerably, but will typically be maintained in a range of about 0° Celsius to the boiling point of the halogenated aromatic reactant. The optimum temperature will vary somewhat, depending on the particular halogenated aromatic compound to be fluorinated. Preferably, in the fluorination of benzotrichloride or hexachloroxylene, the reaction temperature is about 20° to about 75° Celsius. The reactions are preferably carried out at atmospheric pressure, although sub-atmospheric or super-atmospheric pressures may be employed.

The amount of catalyst employed may vary considerably, for example, as high as 5 percent or higher. Higher concentrations may be employed but provide no special advantage and in addition, increase the possibility of polymer formation. Moreover, it is a particular advantage of the catalyst of this invention that the reaction may be effectively carried out with relatively low concentrations of catalyst. Thus, the preferred amount of molybdenum pentachloride catalyst is about 0.01 to about 1.0 percent by weight based on the amount of halogenated aromatic compound. Most preferably, the amount of molybdenum pentachloride catalyst is about 0.02 to about 0.2 percent by weight based on the amount of halogenated aromatic compound.

Typically, the process of this invention is carried out by charging the liquid halomethyl aromatic compound and molybdenum pentachloride catalyst to a reactor and feeding hydrogen fluoride in either the liquid or gaseous state, at a temperature, for example, of about 0° to about 100° Celsius, into the charged reactor. The reaction mixture may be stirred or agitated to provide good contact of the reactants and the catalyst. The reaction may be carried out in a batch process or continuous process. The length of time of the reaction will vary considerably, depending for example, on the strength or concentration of fluorinating agent employed and the degree of fluorination desired.

Many of the common fluorinating agents which will result in the desired reaction, may be employed. However, because of its reactivity and availability, the preferred fluorinating agent is hydrogen fluoride. It is an advantage of this invention that hydrogen fluoride may be employed either in concentrated or dilute form.

It is preferred to carry out the fluorination process of this invention in the absence of a solvent. However, a solvent may be employed, if desired. Typical solvents which may be employed include, for example, aromatic hydrocarbon solvents, such as benzene, or perfluorinated solvents, such as perfluorinated alkanes and the like, which solvents may, in some instances, be added as a reactant.

The amount of hydrogen fluoride employed will vary depending on the degree of fluorination desired. An excess of fluorinating agent may be employed. However, it is a particular advantage of the process of this invention that a large excess hydrogen fluoride is not required. Thus, hydrogen fluoride is preferably employed in an amount of approximately stoichiometric quantities, up to about 15 percent stoichiometric excess, based on the degree of fluorination desired. Thus, for example, when a compound such as benzotrichloride is to be partially fluorinated in accordance with the invention it is preferred to employ less than about 3 moles of hydrogen fluoride per mole of benzotrichloride. Similarly, for the partial fluorination of hexachloroxylene, it is preferred to employ less than about 6 moles of hydrogen fluoride reactant.

In one aspect of this invention, the liquid phase fluorination, utilizing a molybdenum pentachloride catalyst may be combined with a known vapor phase fluorination process to provide a highly effective two step fluorination process wherein improved utilization of hydrogen fluoride is achieved. Vapor phase fluorination processes commonly employ a substantial stoichiometric excess of hydrogen fluoride—typically in the range of a 50 percent excess. As a result, the off-gases from such processes are a mixture of HF and HCl. Dilute HF mixtures of this type are generally ineffective as starting materials in the vapor phase processes and thus are not readily re-cyclable in the process. However, such dilute HF gas mixtures, especially mixtures of HF and HCl, may be employed as the fluorinating agent in the process of this invention. Thus, the process of this invention provides an effective means of utilization of the dilute HF effluent gases of a vapor phase fluorination process.

HF-HCl mixtures, such as the effluent gases from a vapor phase fluorination process may be utilized as fluorinating agents in accordance with this invention either in a separate, independent liquid phase fluorination process or as an additional step, in combination with a vapor phase fluorination process. In the latter case, the HF-HCl off-gases from a vapor phase process may be supplied directly or indirectly to a liquid phase reactor charged with the haloalkyl aromatic compound to be fluorinated and a catalytic amount of molybdenum pentachloride. The haloalkyl aromatic compound is then at least partially fluorinated in the manner hereindescribed so that for example on the average, at least one halogen atom on the haloalkyl side chain is replaced by a fluorine atom. The liquid phase fluorination may be carried out to various degrees of fluorination. Thus, in the liquid phase fluorination step the haloalkyl aromatic may be fully fluorinated or fluorinated to the degree required for a particular product and this fully or partially fluorinated product recovered as the end product. Alternatively, in a preferred embodiment, the haloalkyl aromatic is partially fluorinated in the liquid phase and the partially fluorinated product re-cycled to the vapor phase fluorination step to be more fully fluorinated. As an example of this embodiment, the preparation of p-chlorobenzotrifluoride may be considered. In a simplified overview the process may be described as follows: p-chlorobenzotrochloride is fed into a vapor phase fluorination reactor together with a substantial excess of anhydrous hydrogen fluoride and reacted therein until substantially complete conversion to p-chlorobenzofluoride is achieved. The effluent gas, primarily a mixture of HF and HCl is routed to a liquid phase reactor charged with p-chlorobenzotrichloride and a catalytic amount of molybdenum pentachloride. In the liquid phase fluorination step the p-chlorobenzotrichloride is partially fluorinated to form, for example, a monofluorinated product and/or a difluorinated product. This partially fluorinated product is then filtered and recycled to the vapor phase reactor, and combined with the vapor phase starting material p-chlorobenzotrichloride to be substantially fully fluorinated by reaction with anhydrous HF. The preferred partially fluorinated product of the liquid phase reaction, to be recycled is the monofluorinated product. The final off-gas from this two step process is HCl which may contain minor amounts, such as up to about 10% of HF. The HF may be separated by known means to produce substantially pure HCl, useful in a variety of commercial purposes, such as the production of commercial grade muriatic acid.

The aforementioned "monofluorinated product" and "difluorinated product" refer to products having a corresponding average replacement of halogen atoms by fluorine atoms, even though some molecules may have no halogen atoms replaced while others may have one, two or three halogen atoms replaced. Thus, for example, in the fluorination of benzotrichloride, the monofluorinated product may be a mixture of benzotrichloride ($\alpha,\alpha,\alpha$-trichlorotoluene), benzofluorodichloride ($\alpha$-fluoro-$\alpha,\alpha$-dichlorotoluene, benzodifluorochloride ($\alpha,\alpha$-difluoro-$\alpha$-chlorotoluene) and benzotrifluoride ($\alpha,\alpha,\alpha$-trifluorotoluene) wherein the average replacement for all of the benzotrichloride molecules subject to the fluorination process is approximately one fluorine atom per molecule. In a similar manner, the difluorinated product may refer to a product wherein the average replacement is two fluorine atoms per molecule.

It will be seen that in accordance with the description hereinabove the liquid phase fluorination process of this invention may be employed in the production of partially fluorinated or fully fluorinated haloalkyl aromatic products (the term "fluorinated" referring to fluorine replacements on the haloalkyl side chain); and may utilize as the fluorinating agent either anhydrous HF or dilute HF-HCl mixtures or other fluorinating agents. Furthermore, this liquid phase process may be employed as an independent process or may be employed in a two step process together with a vapor phase fluorination step. One suitable vapor phase reaction that may be employed in combination with the liquid phase process of this invention is described in U.S. Pat. No. 3,859,372, the disclosure of which is incorporated herein by reference. However, other vapor phase processes known in the art may similarly be combined with the liquid phase process of this invention. Thus the partially fluorinated compounds such as A-1, A-II and B-I through B-VIII, and others, which may be prepared in accordance with this invention may be advantegeously employed as starting materials in various other fluorination processes such as the aforementioned vapor phase fluorination processes. In addition, the partially fluorinated compounds may be employed as chemical intermediates for the preparation of various end products, such as pesticides and dyestuffs. In particular, trichloromethyl-trifluoromethyl aromatic compounds, such as compound B-IV, above, are especially useful as chemical intermediates since the trichloromethyl group is readily hydrolyzed to form, for example carboxylic acid or carboxamide derivatives or partially hydrolyzed to form benzoyl chloride derivatives.

The examples set forth hereinbelow will serve to further illustrate the invention and the manner in which it may be practiced. The examples are set forth for purposes of illustration and are not to be construed as limitative of the present invention. Many variations of the process may be made without departing from the spirit and scope of the invention. In the examples, unless otherwise stated, all parts and percentages are by weight and all temperatures are in degrees Celsius.

EXAMPLE 1

A stirred batch steel reactor was charged with 15,436 parts of distilled benzotrichloride (greater than 99% purity) and 23.2 parts of molybdenum pentachloride. The reactor was heated to a temperature in the range of 40° to 60° C. and anhydrous hydrogen fluoride, at a temperature of about 75° C. was bubbled in at a rate of about 15 to 17 parts per minute, with agitation. The effluent gases were passed through a reflux condenser and cold trap to prevent loss of organic materials. The reaction was continued under these conditions with periodic sampling and specific gravity determination of the samples. The effluent gases were analyzed periodically and when HCl evolution ceased the reaction was assumed to be complete. The reaction product was analyzed by gas chromatographic techniques and found to contain 99.4% benzotrifluoride.

EXAMPLE 2

In a continuous liquid phase fluorination, a stream of parachlorobenzotrichloride (96.5% pure), containing 0.05 percent molybdenum pentachloride, was fed into a columnar nickel reactor co-currently with a gaseous mixture of HF and HCl in a molar ratio of about 0.5 HF:HCl. The reaction temperature was maintained between 35° and 55° C. and the flow rate of the reactants was adjusted to provide a retention time of about 3 hours. The reaction was continued for a period of 75 hours during which the progress of the reaction was monitored through periodic sampling and analysis of the reaction mixture and effluent gases. Analysis of the product by gas chromatography indicated the following typical composition in mole percent: chlorobenzotrifluorides, 0.2%; p-chloro-$\alpha$-fluoro-$\alpha,\alpha$-dichlorotoluene, 12.0%; p-chloro-$\alpha,\alpha$-difluoro-$\alpha$-chlorotoluene, 39.0%, parachlorobenzotrichloride, 43.0%; others, 5.8%.

The product collected during the reaction was filtered and fed to a vapor phase fluorinator of the type described in U.S. Pat. No. 3,859,372 where it was further reacted with anhydrous hydrogen fluoride. In the vapor phase fluorinator, anhydrous hydrogen fluoride was supplied to the reaction in an amount of about 3 moles of HF per mole of organic feed. The final product of the vapor phase reaction step contained greater than 95% parachlorobenzotrifluoride.

EXAMPLE 3

A mixture of 29,860 parts of parachlorobenzotrichloride and 2.968 parts of molybdenum pentachloride was charged to a nickel reaction vessel and heated to 50° C. (The parachlorobenzotrichloride feed was 95% pure, and contained about 5% of metachloro-, and orthochloro-isomers and higher chlorinated materials). The temperature was maintained at about 50° C. and the reactor contents were stirred continuously while a gaseous mixture of hydrogen fluoride and hydrogen chloride was sparged into the reactor over a period of 10 hours and 20 minutes. The gaseous mixture was composed of about 33 mole percent of HF and 67 mole percent of HCl and was representative of the effluent gas from a catalytic vapor phase fluorination process wherein 4.5 moles of HC is supplied per mole of parachlorobenzotrichloride. The feed rate of HF was 1.45 parts per minute. Samples of the reaction mixture and the HCl effluent gas were withdrawn periodically and analyzed. Completion of the reaction was indicated by the cessation of HCl evolution. The final product was analyzed by gas chromatography and found to contain 97.5 percent parachlorobenzotrifluoride.

EXAMPLE 4

Parachlorobenzotrichloride was fluorinated as in Example 3 except that the reaction was carried out on a continuous basis over a 54 hour period as follows: the parachlorobenzotrichloride, containing 0.1 percent molybdenum chloride was fed to the reactor at a rate of 4.94 parts per minute. The HF-HCl mixture was fed to the reactor at a rate of 1.45 parts per minute, based on HF (about 10 percent above the stoichiometric amount. The feed rates of the reactants were such as to allow a 10 hour residence time. The composition of the HF feed gas varied between an HF:HCl molar ratio of about 1:2 and 1:3. Analysis of the reaction product over a 54 hour period indicated an average composition of about 92 percent parachlorobenzotrifluoride.

EXAMPLES 5-12

In Examples 5-10 a mixture of 583 parts of benzotrichloride (BTC) and 0.583 parts of molybdenum pentachloride was charged to a Teflon reaction vessel and heated to about 50° C. Hydrogen fluoride, at a temperature of about 70° C. was cooled slightly and bubbled into the reactor. The temperature was maintained at about 50° C. and the reaction mixture was stirred, while the hydrogen fluoride was introduced slowly at the rate and total amount shown in the Table I below. Product samples were stirred over soda ash, filtered and the percent benzotrifluoride (BTF) was determined by gas chromatography with the results as shown in the Table.

For purposes of comparison, in Example 11 the procedure was repeated except that the reactor was not heated, no catalyst was employed, and the reaction mixture was exposed to ultraviolet radiation from a 100 watt mercury lamp laced about one inch from the reactor wall.

Also for purposes of comparison, in Example 12, the procedure of Examples 5-10 was repeated except that no molybdenum pentachloride catalyst was employed.

TABLE I
MoCl$_5$ Catalyzed BTC to BTF Reactions

| Example | Weight % of MoCl$_5$ Catalyst | BTC (parts) | BTF (%) | Time of Reaction | HF Flow (parts/min.) | % Excess HF | Reactor Temp °C. | Total HF Introduced (parts) |
|---|---|---|---|---|---|---|---|---|
| 5 | 0.10 | 583 | 97.5 | 5 hr. 10 min. | 0.64 | 12% | 50°-55° | 200 |
| 6 | 0.10 | 583 | 98.1 | 2 hr. 45 min. | 1.48 | 36% | 50°-70° | 244 |
| 7 | 0.10 | 583 | 97.2 | 1 hr. 50 min. | 1.77 | 10% | 50°-60° | 195 |
| 8 | 0.10 | 583 | 98.4 | 1 hr. 35 min. | 1.93 | 3% | 50°-60° | 183 |
| 9 | 0.10 | 583 | 98.5 | 1 hr. 11 min. | 2.70 | 8% | 50°-53° | 192 |
| 10 | 0.10 | 583 | 95.4 | 48 min. | 4.65 | 25% | 50°-60° | 223 |
| 11 (U.V.) | — | 583 | 3.0 | 3 hr. 5 min. | 1.62 | 167% | 15°-25° | 300 |
| 12 | — | 583 | 3.5 | 3 hr. 20 min. | 1.64 | 183% | 15°-25° | 328 |

EXAMPLE 13

A mixture of 62.6 parts of 3-bis-(trichloromethyl)benzene and 1.0 part of molybdenum pentachloride was heated to about 60° C. and maintained thereat, with stirring, while hydrogen fluoride was bubbled into the mixture at a rate of about 0.077 parts per minute until a total of about 12.0 parts of the hydrogen fluoride had been added. The mixture was stirred for an additional hour. The reaction product was analyzed by gas chromatographic techniques and found to contain the following:

| Product | % |
|---|---|
| 1,3-bis-(trichloromethyl)benzene | 9.0 |
| 1-trichloromethyl-3-(dichloro-fluoromethyl)benzene | 6.3 |
| 1-trichloromethyl-3-(chloro-difluoromethyl)benzene | 38.6 |
| 1,3-bis-(dichloro-fluoromethyl)benzene | 1.4 |
| 1-trichloromethyl-3-trifluoromethyl benzene | 14.7 |
| 1-(dichloro-fluoromethyl)-3-(chloro-difluoromethyl)benzene | 1.6 |
| 1-(dichloro-fluoromethyl)-3-(trifluoro-methyl)benzene | 22.1 |
| 1,3-bis-(chloro-difluoromethyl)benzene | 1.1 |
| 1-(chloro-difluoromethyl)-3-trifluoro-methyl benzene | 1.1 |
| 1,3-bis-(trichloromethyl)benzene | trace amount |

What is claimed is:
1. A process for the preparation of compounds of the formula

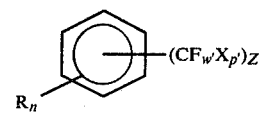

comprising contacting a compound or mixture of compounds of the formula

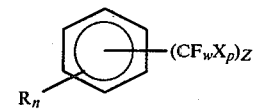

in the liquid phase, with hydrogen fluoride in the presence of molybdenum pentachloride wherein
Z is 1 or 2
each R is selected from the group consisting of aryl, substituted aryl, halogen, alkyl, alkoxy, substituted alkyl, and substituted alkoxy;
n is 0 to 5;
X is a halogen atom other than fluorine;
the maximum value of n+Z is 6;
w+p is 3;
w'+p' is 3;
with the proviso that
when Z is 1:
w is 0 to 1
p is 2 to 3
w' is 1 to 2, and is greater than w;
p' is 1 to 2, and is less than p;
and, when Z is 2:
the total value of w is 0 to 4
the total value of p is 2 to 6
the total value of w' is 1 to 5 and is greater than w
the total value of p' is 1 to 5 and is less than p.
2. A process according to claim 1 wherein X is chlorine.
3. A process according to claim 2 wherein R is chlorine and n is 0 to 2.
4. A process according to claim 3 wherein Z is 2.
5. A process according to claim 4 wherein n is 0.
6. A process according to claim 5 wherein the total value of p' is 1 and w' is 5.
7. A process according to claim 5 wherein the total value of p' is 2 and w' is 4.
8. A process according to claim 5 wherein the total value of p' is 3 and w' is 3.

9. A process according to claim 5 wherein the total value of p' is 4 and w' is 2.

10. A process according to claim 5 wherein the total value of p' is 5 and w' is 1.

11. A process for the preparation of compounds of the formula

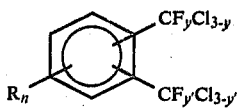

wherein each R is selected from the group consisting of aryl, substituted aryl, halogen, alkyl, alkoxy, substituted alkyl, and substituted alkoxy; n is 0 to 4; y and y' independently, each have an average value of 0 to 3; and the total value of y+y' is 1 to 5; which comprises contacting a compound of the formula

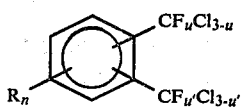

wherein R is as defined above; u and u' independently each have an average value of 0 to 3, and the total value of u+u' is 0 to 4, and the total value of u+u' is less than the total value of y+y'; with less than 6 moles of hydrogen fluoride in the presence of molybdenum pentachloride.

12. A process according to claim 11 wherein R is chlorine.

13. A process according to claim 11 wherein n is 0.

14. A process according to claim 13 wherein u and u' are each 0.

15. A process according to claim 14 for the preparation of a compound of the formula

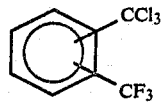

which comprises contacting a compound of the formula

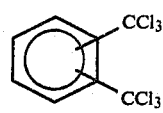

with hydrogen fluoride in the presence of molybdenum pentachloride.

16. A process for the preparation of a trichloromethyl-trifluoromethylbenzene of the formula

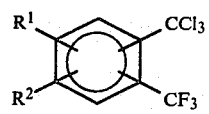

where $R^1$ and $R^2$ are independently selected from the group consisting of hydrogen, fluorine, chlorine and bromine which comprises contacting a bis-(trichloromethyl)-benzene of the formula

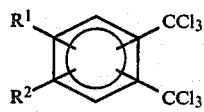

wherein $R^1$ and $R^2$ have the previously assigned significance with less than 6 mole of hydrogen fluoride per mole of bis-(trichloromethyl)-benzene in the presence of a molybdenum pentachloride catalyst.

* * * * *